(12) United States Patent
Tappert et al.

(10) Patent No.: US 11,572,780 B2
(45) Date of Patent: Feb. 7, 2023

(54) PARAFFIN INHIBITOR PERFORMANCE

(71) Applicant: The University of Tulsa, Tulsa, OK (US)

(72) Inventors: Marc Tappert, Bartlesville, OK (US); Dale Teeters, Sand Springs, OK (US)

(73) Assignee: The University of Tulsa, Tulsa, OK (US)

( * ) Notice: Subject to any disclaimer, the term of this patent is extended or adjusted under 35 U.S.C. 154(b) by 393 days.

(21) Appl. No.: 16/859,615

(22) Filed: Apr. 27, 2020

(65) Prior Publication Data

US 2020/0355062 A1    Nov. 12, 2020

Related U.S. Application Data

(60) Provisional application No. 62/844,342, filed on May 7, 2019.

(51) Int. Cl.
*E21B 37/06* (2006.01)
*E21B 47/00* (2012.01)
*G01N 27/06* (2006.01)
*G01N 33/24* (2006.01)
*C09K 8/524* (2006.01)

(52) U.S. Cl.
CPC .......... *E21B 47/006* (2020.05); *G01N 27/06* (2013.01); *G01N 33/241* (2013.01); *C09K 8/524* (2013.01)

(58) Field of Classification Search
CPC ....... C09K 8/524; E21B 37/06; E21B 47/006; G01N 27/026; G01N 27/06; G01N 33/241
See application file for complete search history.

(56) References Cited

U.S. PATENT DOCUMENTS

| | | | |
|---|---|---|---|
| 7,575,789 B2 * | 8/2009 | McKeen | F16L 9/121 |
| | | | 138/146 |
| 9,347,009 B2 * | 5/2016 | Kusinski | C10L 1/04 |
| 10,344,229 B2 * | 7/2019 | Balashanmugam | C10G 75/00 |

* cited by examiner

*Primary Examiner* — Vinh P Nguyen
(74) *Attorney, Agent, or Firm* — McAfee & Taft

(57) ABSTRACT

Impedance is used to determine the performance of paraffin inhibitors in oil containing paraffin. The method and system can use a specially designed impedance cell having a cell constant of less than 1 cm$^{-1}$. Further, the method can include obtaining at least impedance measurements above the wax appearance temperature (WAT) for an oil sample treated with a paraffin inhibitor and an oil sample not treated, and impedance measurements below the WAT for the treated oil sample and the untreated oil sample. Thereafter, the impedance measurements are correlated to determine paraffin inhibitor performance.

9 Claims, 8 Drawing Sheets

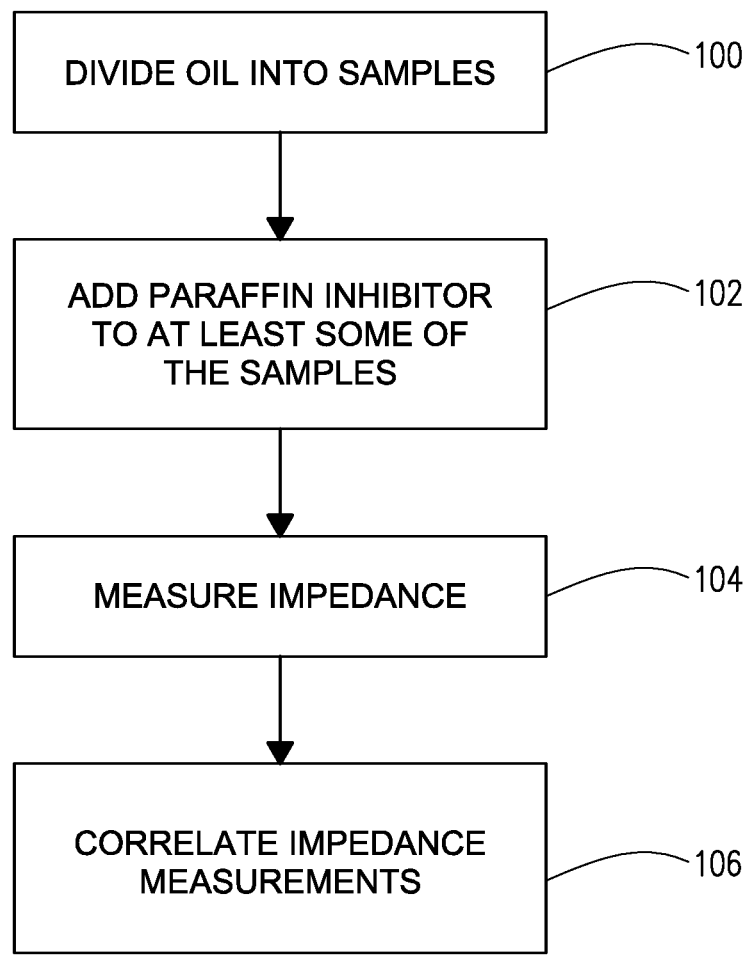

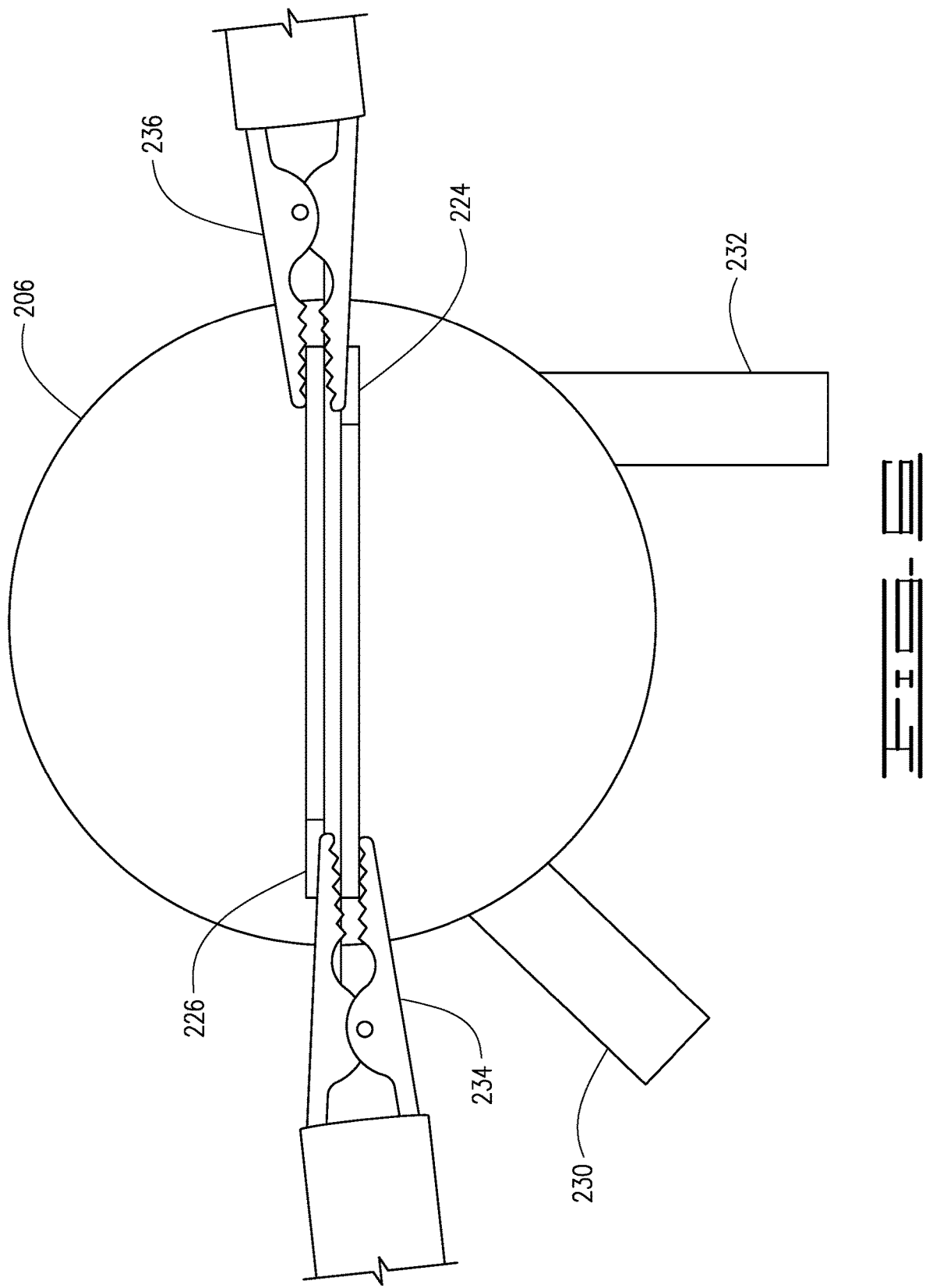

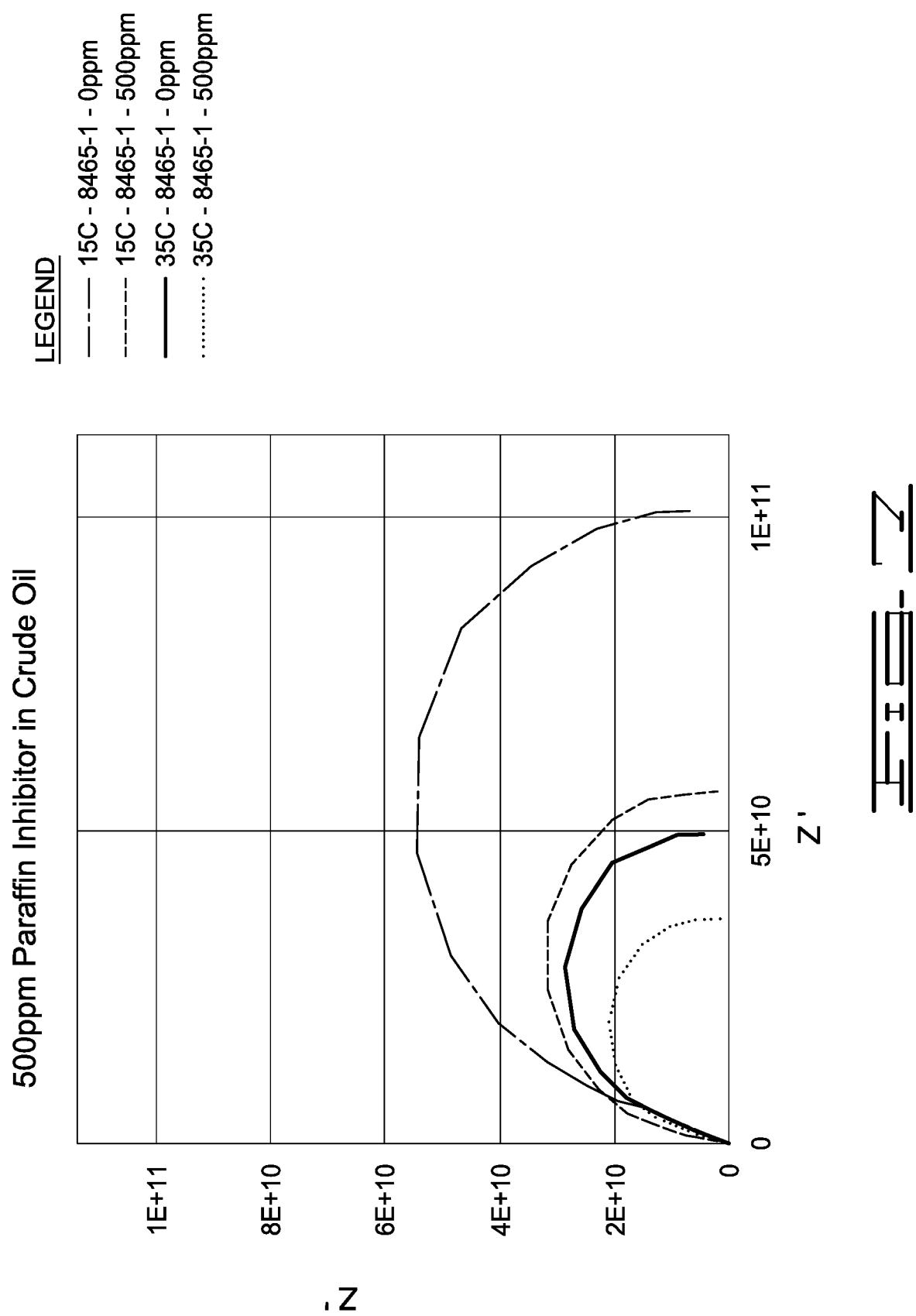

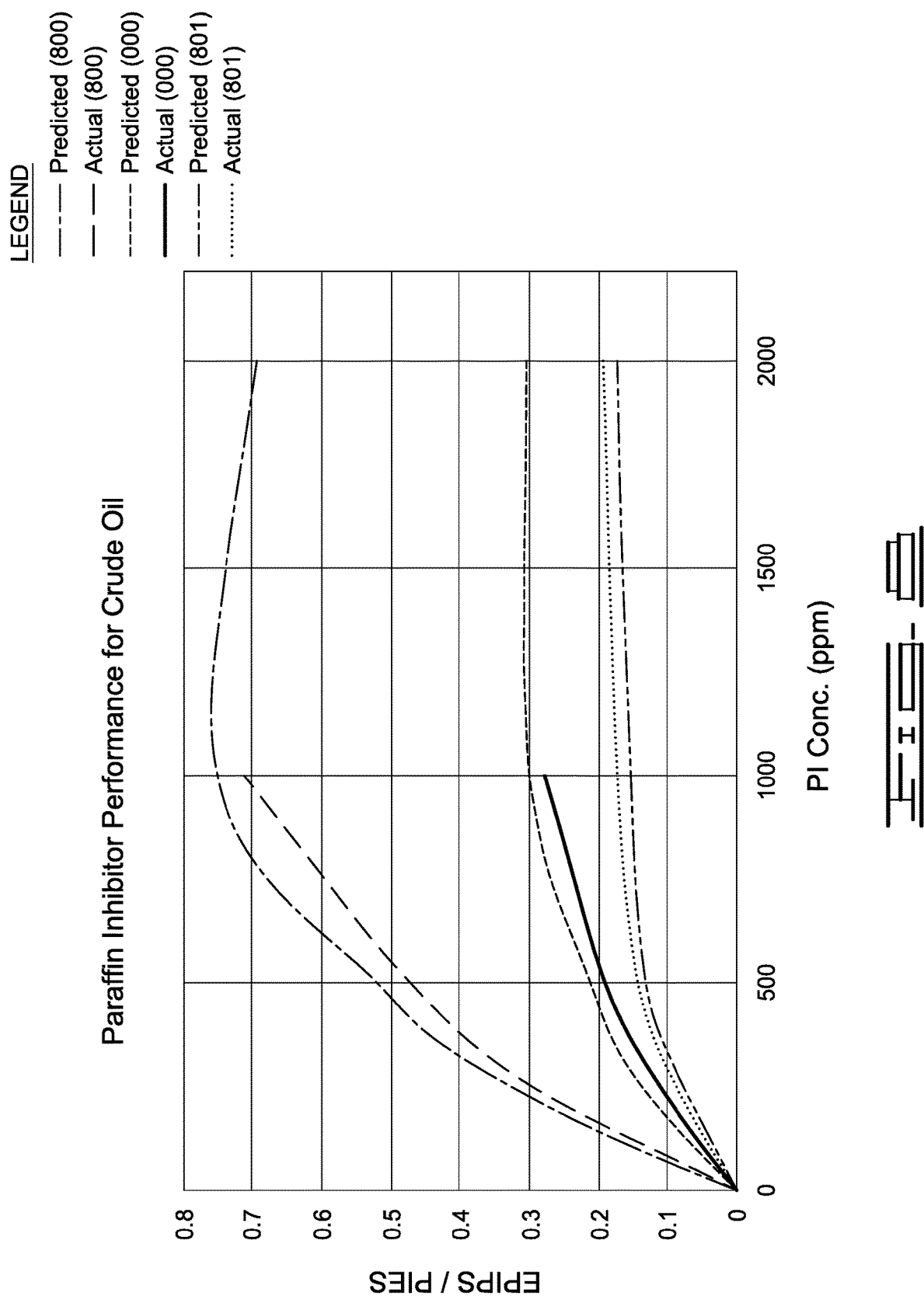

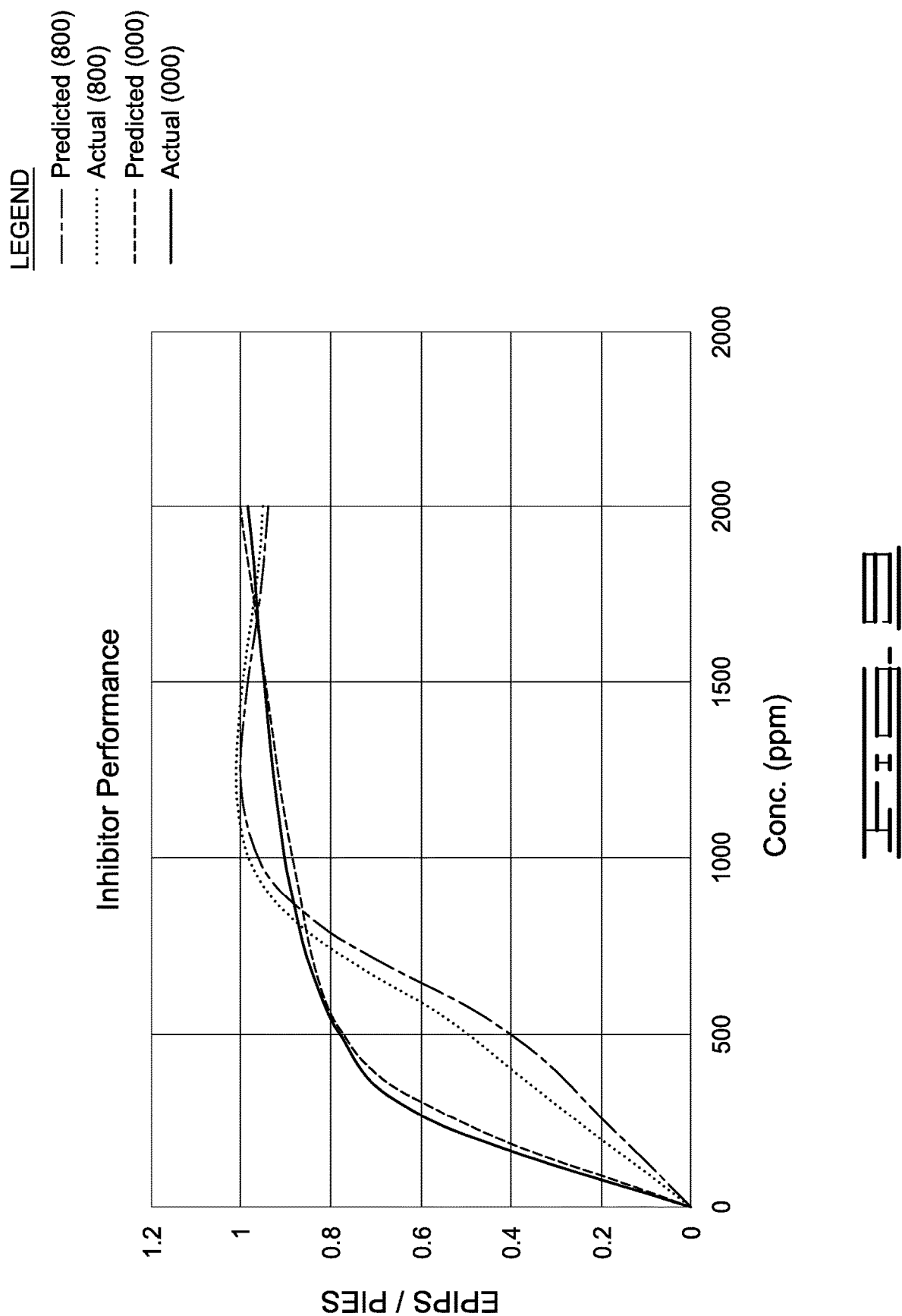

PARAFFIN INHIBITOR PERFORMANCE

CROSS-REFERENCE TO RELATED APPLICATION

This application claims the benefit of U.S. Provisional Patent Application No. 62/844,342 filed on May 7, 2019, which is hereby incorporated by reference.

FIELD

This disclosure relates generally to reducing paraffin deposits in fluids from oil and gas wells, and more particularly, to evaluating the performance of paraffin inhibitors in reducing paraffin deposits.

BACKGROUND

In the course of oil production, temperature and pressure changes result in the crystallization of paraffin molecules, which are a constituent of the crude oil and of the crude oil raffinates. Owing to this crystallization process, these paraffins can be deposited in production bores, delivery probes, pipelines or plant parts, such as tanks, which can be disadvantageous for the productivity in the oil extraction and in the oil storage or the transport. Moreover, the crystallization of the paraffin molecules when the temperature goes below the pour point leads to the solidification of the crude oil. In that case, the oil can no longer be transported, which has the consequence that the oil production can come to a standstill.

To prevent such paraffin deposits or the solidification of the oil, generally paraffin inhibitors or pour point depressants are added to the corresponding systems. In general, the paraffin inhibitors and pour point depressants consist of polymeric structures, which can be in an organic solvent.

In order to test the efficiency of paraffin inhibitors, conventionally a "cold finger test" is utilized. In the cold finger test, the test system has a metal surface (finger) which is submerged in the oil. The oil is heated to slightly below the temperature at which the paraffins crystalize, referred to as the wax appearance temperature (WAT). The finger is cooled to well below the WAT. The thermal gradient in the oil creates a driving force that causes the paraffins to crystalize and deposit on the cold finger surface. This experiment is typically conducted using a range of paraffin inhibitor concentrations, such as ranging from 0 to 2000 ppm. Unfortunately, the cold finger test requires significant time to run. Generally, the minimum time to run a cold finger test is four hours, but more typically, such a test requires 16 or more hours.

Accordingly, the oil and gas industry is interested in alternative ways to accurately and quickly determine the performance of paraffin inhibitors.

SUMMARY OF THE INVENTION

Embodiments of this disclosure relate to systems and methods of using impedance to determine the performance of paraffin inhibitors in oil containing paraffins. The oil of concern will often be a crude oil but the system and methods are generally applicable to hydrocarbons that have high impedance.

More specifically, in some embodiments there is provided a method comprising:

measuring impedance of an oil containing a paraffin so as to obtain at least four impedance measurements, wherein the impedance measurements include:

a BT impedance measurement, wherein the BT impedance measurement is for a treated sample of the oil sample which contains a paraffin inhibitor, and wherein the impedance is measured at a first temperature below the wax appearance temperature (WAT) of the paraffin;

a BN impedance measurement, wherein the BN impedance measurement is for a neat sample of the oil which does not contain the paraffin inhibitor, and wherein the impedance is measured at the first temperature;

an AT impedance measurement, wherein the AT impedance measurement is for the treated sample, and wherein the impedance is measured at a second temperature above the WAT of the paraffin; and an AN impedance measurement, wherein the AN impedance measurement is for the neat sample, and wherein the impedance is measured at the second temperature;

determining from the impedance measurements a set of impedance values which allows for comparison so as to determine paraffin inhibitor performance; and comparing the set of impedance values to determine paraffin inhibitor performance.

For example, the set of impedance values can be determined by normalizing one or more of the impedance measurements. The normalization allows for comparison by compensating for changes to impedance caused by temperature change, by introduction of paraffin inhibitor or by both. After normalization, the impedance values in the normalized set are compared to determine paraffin inhibitor performance.

Typically, the impedance can be measured by potentiometric electrochemical impedance spectroscopy (EIS). Because of the high impedance of the oil, the EIS measurements will generally be conducted using a special EIS cell, such as the one described below.

In the method, normalization can be carried out by normalizing the AN impedance measurement and normalizing the AT impedance measurement relative to a ratio of the BN impedance measurement and AN impedance measurement to compensate for temperature, and normalizing the BT impedance measurement relative to a ratio of the AN impedance measurement and AT impedance measurement to compensate for paraffin inhibitor introduction.

Typically, the method will use multiple treated samples of the oil with each such sample having a different concentration of paraffin inhibitor and wherein the BT impedance and AT impedance are measured for each of the treated samples. The comparison results in a predicted paraffin performance for each concentration of paraffin inhibitor to produce a set of predicted paraffin performances. The predicted paraffin performances are analyzed to determine an optimal concentration of paraffin inhibitor for the oil. Further, the analysis can be by curve fitting.

In accordance with some embodiments, a special EIS cell is used to conduct the EIS measurements. The EIS cell can comprise a top wall, a bottom wall, an outer wall and an inner wall. The outer wall extends from the bottom wall to the top wall. The inner wall is interior to the outer wall such that the top wall, the bottom wall, the outer wall and the inner wall form a first chamber extending between the inner wall and the outer wall and beneath the inner wall. The first chamber is configured to contain a flowing fluid with fluid flow, such as for temperature control of the cell, into and out of the first chamber through an upper port and a lower port. Further, the inner wall defines a second chamber having an access port through the top wall. The second chamber is formed from a first flat surface of the inner wall and a second flat surface of the inner wall with the first flat surface opposing the second flat surface. The first flat surface and the second flat surface are configured to have a size and separation so as to contain a volume of test fluid and two electrically conducting plates such that the EIS cell has a cell constant of less than 1 cm$^{-1}$.

For example, the cell constant of less than 1 cm$^{-1}$ can be achieved by having the first flat surface spaced apart from the second flat surface by a distance of 0.5% or less—and more typically 0.1% or less—of the lesser of the surface area of the first flat surface or the surface area of the second flat surface. The EIS cell would include two conducting plates aligned with the first and second flat surfaces and of similar size, shape and spacing so as to obtain the cell constant of less than 1 cm$^{-1}$. Thus, the two parallel electrically-conducting plates are introduced into the second chamber such that the two conducting plates are spaced apart by a distance of less than 0.5% or less of the surface area of either of the first flat surface or the second flat surface. A test fluid is introduced into the second chamber, and the impedance of the test fluid is measured by introducing a current to the conducting plates.

The outer wall can define the upper port and the lower ports with the upper port positioned higher on the outer wall than the lower port. Typically, the upper port and lower port are configured so that fluid is introduced through either the upper port or lower port tangentially to the outer wall. Also, the upper port and lower port can be spaced about the outer wall so as not to be in vertical alignment.

Another embodiment is directed to a method of measuring impedance. The method comprises providing a testing cell in accordance with one of the above embodiments. Subsequently, a first fluid is introduced through a first port (which can be the upper or lower port) into the first chamber such that the first fluid exits out of the first chamber through a second port (which can be the upper or lower port) thus flowing the first fluid through the first chamber and controlling the temperature within the second chamber by the flow of the first fluid.

BRIEF DESCRIPTION OF THE DRAWINGS

FIG. 1 is a flow diagram illustrating the method of the current disclosure.

FIG. 6 is a top view picture of the EIS cell of FIG. 4.

FIG. 7 is a Nyquist plot of impedance for a neat sample and a treated sample containing 500 ppm of a paraffin inhibitor.

FIG. 8 is a graph of paraffin inhibitor performance in a crude oil. FIG. 8 illustrates cold finger testing (actual) and predicted results made by a method in accordance with this disclosure.

FIG. 9 is a graph of paraffin inhibitor performance in a light-shale crude condensate. FIG. 9 illustrates cold finger testing (actual) and predicted results made by a method in accordance with this disclosure.

DESCRIPTION

Figure 2:
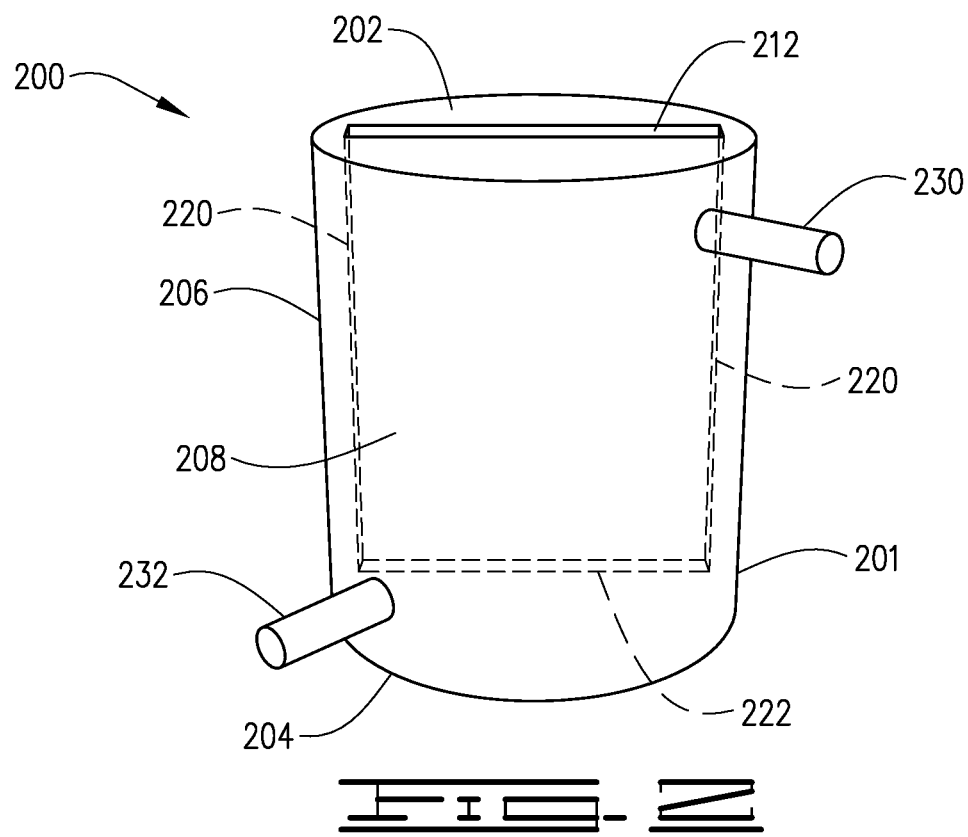
FIG. 2 is a schematic illustration of a front view of an EIS cell in accordance with some embodiments of this disclosure.
Figure 3:
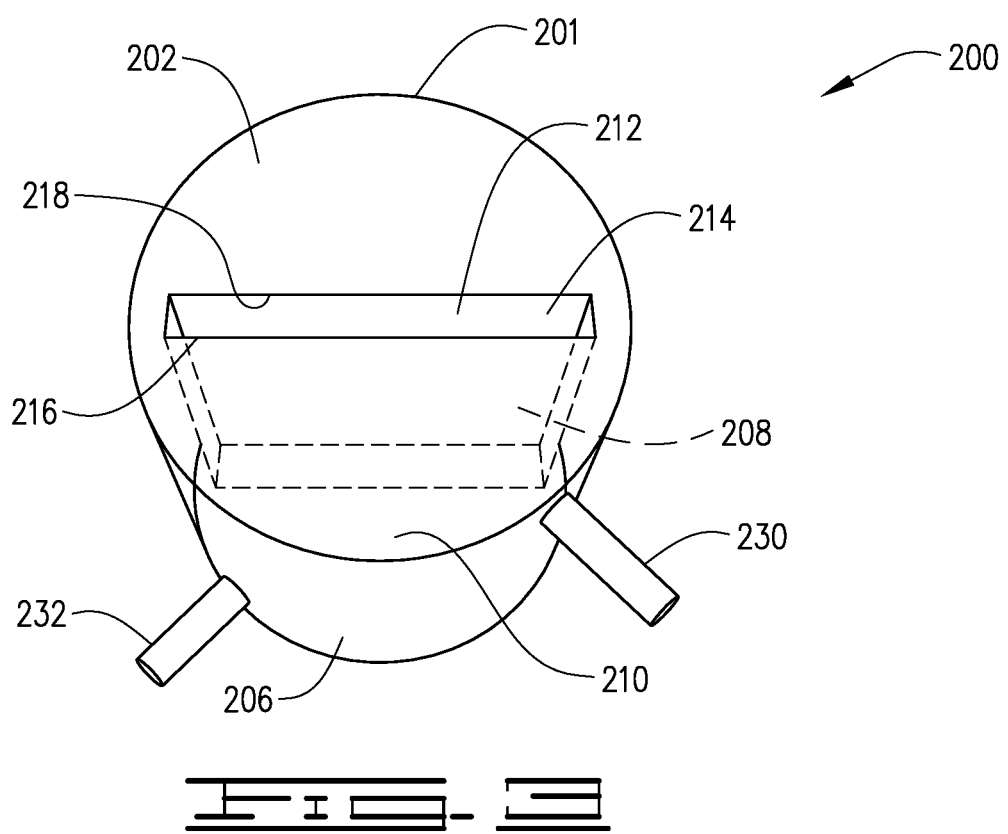
FIG. 3 is a schematic illustration of a top view of the EIS cell of FIG. 2.

The present disclosure may be understood more readily by reference to the following description. In addition, numerous specific details are set forth in order to provide a thorough understanding of the embodiments described herein. However, those of ordinary skill in the art will understand that the embodiments described herein can be practiced without these specific details. In other instances, methods, procedures and components have not been described in detail so as not to obscure the related relevant feature being described. Additionally, the description is not to be considered as limiting the scope of the embodiments described herein.

In the drawings, various embodiments are illustrated and described wherein like reference numbers are used herein to designate like elements throughout the various views. The figures are not necessarily drawn to scale, and in some instances the drawings have been exaggerated and/or simplified in places for illustrative purposes only. Where components of relatively well-known designs are employed, their structure and operation will not be described in detail. One of ordinary skill in the art will appreciate the many possible applications and variations of the present invention based on the following description.

This disclosure relates to systems and methods of using electrical impedance to determine the performance of paraffin inhibitors in oil containing paraffin. The oil of concern will often be a crude oil but the system and methods are generally applicable to hydrocarbons that have high impedance. For example, "high impedance" generally corresponds to values of greater than about $10^7$ ohms, typically greater than about $10^9$ ohms, such as values from $10^9$ ohms to $10^{12}$ ohms. For comparison, traditional electrolytic solutions (for example, 0.1 M KCL) and seawater have impedance values corresponding to values on the order of $10^{-2}$ to $10^2$ ohms.

Most conventional technology for measuring paraffin inhibitor performance in oils rely in the cold finger test, which typically requires a minimum of four hours, and more typically 16 or more hours, to estimate paraffin inhibitor performance. Generally, the conventional systems for measuring paraffin performance require at least three times the quantity of oil for analysis as are required for the systems of the current disclosure.

The systems and methods of this disclosure are based upon measuring the electrical impedance of the oil with and without paraffin inhibitors. Generally, the impedance will be measured for an oil sample without a paraffin inhibitor and for one or more samples of the oil having a paraffin inhibitor added. Typically, there will be at least three samples of the oil having a paraffin inhibitor and the samples will all have varying concentrations of the paraffin inhibitors. For each sample, the impedance will be measured at two or more temperatures; however, typically two temperatures are sufficient with one being selected to be above the paraffin crystallization temperature—the wax appearance temperature (WAT)—and one being selected to be below the WAT. The WAT, also known as the cloud point, is defined as the temperature at which paraffin first precipitates. In the petroleum industry, such wax depositions in pipelines and reservoirs can lead to many issues, including a reduced flow or even a blocked pipeline, with subsequent important production problems.

Turning now to FIG. 1, the method of this disclosure will be further described. In step 100 of FIG. 1, a paraffin containing oil is divided into two or more samples. While it is possible to carry out the process with three samples or even just two samples, this limits the analysis of the paraffin inhibitor performances as will be realized from the discussion below. Accordingly, it is preferable to divide the paraffin containing oil into four or more samples. As will be realized by those skilled in the art, paraffin as used herein is an acyclic saturated hydrocarbon, which can be branched or unbranched and will typically have from 18 carbon atoms to 80 carbon atoms (C18-C80).

Next in step 102, a paraffin inhibitor is added to one or more of the samples to create one or more treated oil samples. However, at least one sample does not have the addition of the paraffin inhibitor so that there is an untreated or neat oil sample. Additionally, the other samples can have varying amounts of the paraffin inhibitor.

The paraffin inhibitors of this disclosure are chemicals added to oil to prevent or minimize paraffin deposition. The paraffin inhibitors have polar functional groups. For example, the paraffin inhibitors can comprise one or more polymers (typically 10,000 MW or lower) with a polar functional group, and a non-polar organic solvent or a mixture of non-polar, organic solvents. The active component (polymer) is typically between one to five percent of the polymer inhibitor and the remainder is the solvent(s). While not wishing to be bound by theory, it is believed that paraffin inhibitors function by binding with the paraffin through Van der Waals forces. For Van der Waals forces to act on an atom or molecule, they must be between 0.3 nm and 0.6 nm from each other. For this reason, selecting the correct polymer is crucial to paraffin inhibitors' function. Bulky side groups can prevent the polymer from bonding with the alkanes, but too small a side group without a polar component typically will not prevent crystal formation and can increase paraffin crystal formation. Alkanes in the molecular weight range classified as paraffins bond together and form hexagonal or orthorhombic crystals which precipitate out of solution when the oil can no longer solubilize them. The polar groups on the polymer disrupt the typical crystal structure that these alkanes form. Thus, the paraffin inhibitors keep these crystals from forming or keep them small enough that they don't precipitate out of the crude oil.

Once the samples are prepared, their electrical impedance is measured in step 104. While any suitable method can be used to measure impedance, potentiometric electrochemical impedance spectroscopy (EIS) is presently preferred and the below discussion will be with regard to EIS—also known as AC Impedance; although, those skilled in the art will be able to readily adapt the principles herein to other impedance measurement systems. When using EIS, the impedance can result in a complex value as the impedance. An absolute value can be obtained such as by use of a Nyquist plot, as further illustrated in the Example below.

To analyze the samples for paraffin inhibitor performance, the impedance is measured for each sample at two different temperatures in step 104. A temperature above and below the WAT of the untreated oil is selected. As is known in the art, the WAT can be measured using a micro differential scanning calorimeter. Once the WAT is determined, an appropriate set of temperatures can be selected. While any suitable set of temperatures above and below the WAT can be selected, generally the temperatures will be from 2° C. to 20° C. above/below the WAT, more typically from 5° C. to 15° C. above/below the WAT. Thus, for each sample, impedance is measured at a first temperature below the WAT and at a second temperature above the WAT.

Next, each of the impedance measurements for each treated sample is correlated with the impedance measurements for the untreated samples to obtain a single indicator (EPIPS value) of paraffin performance for each concentration of paraffin inhibitor, step 106. Thus, at each concentration, a data set is comprised of a test above the WAT with no chemical added, referred to as Above-Neat (AN), a test below the WAT with no chemical added, referred to as Below-Neat (BN), and two more tests at the same temperatures with a given concentration of a paraffin inhibitor, referred to as Above-Treated (AT) and Below-Treated (BT). As will be apparent from this disclosure, for each such data set the two parameters which are varied are temperature and chemical concentration. This leads to one complete data set for each concentration of paraffin inhibitor representing four test conditions and resulting in an AN impedance measurement, a BN impedance measurement, an AT impedance measurement and a BT impedance measurement. Each of these data sets can be used to obtain the EPIPS value.

The correlation of the impedance measurements for each treated sample with the untreated sample typically involves normalization of the measurements. The normalization allows for comparison by compensating for changes to impedance caused by temperature change, by introduction of paraffin inhibitor or by both.

For example, normalization can be carried out by normalizing the AN-impedance measurement by a ratio of the BN-impedance measurement and AN-impedance measurement to compensate for temperature (AN*=AN(BN/AN), where AN* is the normalized AN-impedance measurement, BN is the BN-impedance measurement, and AN is the AN-impedance measurement). As will be realized, this normalization equates the AN-impedance with the BN-impedance. Similarly, the AT-impedance measurements can be normalized by the ratio of the BN-impedance measurement and AN-impedance measurement to compensate for temperature (AT*=AT(BN/AN), where AT* is the normalized AT-impedance measurement and AT is the AT-impedance measurement). Finally, the BT-impedance measurement can be normalized by a ratio of the AN-impedance measurement and AT-impedance measurement to compensate for paraffin inhibitor introduction (BT*=BT(AN/ΔT), wherein BT* is the normalized BT-impedance measurement and BT is the BT-impedance measurement).

The normalized values of a data set are then compared to derive the EPIPS value, which is indicative of the paraffin inhibitor performance at the particular concentration of the data set. For example, an EPIPS value can be derived from the change between the difference in treated and untreated impedance above the WAT (ΔA) and the difference in treated and untreated impedance below the WAT (ΔB). Using percent differences:

$$\Delta A = \text{abs}(AN^* - AT^*)/((AN^* + AT^*)/2); \text{ and}$$

$$\Delta B = \text{abs}(BN - BT^*)/((BN + BT^*)/2).$$

Then, the EPIPS value is:

$$EPIPS = \Delta A - \Delta B$$

Thus, an EPIPS value is found for each concentration of paraffin inhibitor tested. From this set of EPIPS values, the paraffin inhibitor performance can be determined by various numerical analysis techniques known in the art. For example, curve fitting can be used to determine a curve fitting the EPIPS values. The resulting curve can be used to determine EPIPS values for paraffin concentrations other than those tested and can be used to determine where the curve peaks (where the slope of the curve is zero), which equates to the paraffin inhibitor concentration where the paraffin inhibitor has bound all possible paraffins in the system below the WAT. Thus, the optimal amount of paraffin inhibitor to use can be determined.

Measuring impedance—such as by EIS—in the above process is challenging due to the extremely high impedance/resistance of the oil. For example, crude condensate, or condensate for short, represents an area of high interest for establishing paraffin inhibitor performance. "Condensate" refers to the oil produced from unconventional reservoirs through fracking. The primary difference between condensates and "typical" crude oils is primarily in the carbon number distribution present in the oil. Generally, typical black, crude oil will have a larger percentage of large, or heavy, alkane chains, other large molecules, as well as impurities such as silica, salts, and water. Conversely, condensates tend to hold little water, or other impurities, due to the relatively high percentage of short, or light, alkanes. Condensates generally have few or no conductive molecules, such as ions or other polar compounds. Table 1 lists exemplary physical properties of crude oils and condensates.

TABLE 1

| Sample Type | WAT (° C.) | Viscosity at 25° C. (cP) | Density at 25° C. (g/cm$^3$) | Water Content (ppm) | Resistance (Ohms) |
| --- | --- | --- | --- | --- | --- |
| Crude Oil | 27.5 | 4.2850 | 0.8261 | 328 | 9.60E08 |
| Condensate A | 27.9 | 1.6554 | 0.7685 | 19 | 2.97E09 |
| Condensate B | 33.6 | 1.4004 | 0.7650 | 12 | 3.15E09 |

The aforementioned properties, which are characteristic of condensates, lead to them being highly non-conductive, and resistive, and are thus significantly more challenging to measure through electrochemical methods, when compared to crude oils. Additionally, model oils used to understand oil systems typically do not include the impurities; thus, generally, the model systems used in the oil industry are more resistive than their produced counterparts. To measure impedance for crude oils, condensates, and model oils, it is necessary to have an instrument which is capable of measuring ultra-low capacitance, ultra-high resistance, and which has high sensitivity. Conventional cell designs for EIS measurements have been inadequate to meet the needs of measuring impedance in oils.

Turning now to FIGS. 2 to 6, an example of cell design for ultra-low capacitance and ultra-high resistance EIS measurements is illustrated. Cell 200 is suitable for meeting the needs of EIS measurements on ultra-high resistance fluids, such as crude oil and/or condensate. Accordingly, cell 200 has been designed to have a cell constant of less than 1 cm$^{-1}$, as further explained below.

Cell 200 comprises a housing 201 having a top wall 202, a bottom wall 204 and an outer wall 206 extending from bottom wall 204 to top wall 202. Further, cell 200 has an inner wall 208, which is interior to the outer wall such that top wall 202, bottom wall 204, outer wall 206 and inner wall 208 form a first chamber 210. As can be seen from the figures, first chamber 210 extends between inner wall 208 and outer wall 206, and beneath inner wall 208 so as to surround inner wall 208, except at the top where an orifice or access port 212 is formed allowing access to a second chamber 214 defined by inner wall 208.

This second chamber 214 is configured for impedance test so as to be able to contain a test fluid and two electrically conducting plates. As can be seen, second chamber 214 is formed from the inner surfaces of inner wall 208 and is at least partially defined by opposing first flat surface 216 and second flat surface 218. First and second flat surface 216 and 218 are designed to have a large surface area with relatively small separation. Generally, first flat surface 216 can be spaced apart from second flat surface 218 by a distance of 0.5% or less of the lesser of the surface area of either of the first flat surface 216 or the second flat surface 218, or 0.1% or less, 0.05% or less, 0.01% or less, or even 0.005% or less. Although expressed as "the lesser of the surface area", the first flat surface 216 and second flat surface 218 typically have the same size and shape; hence, they have the same surface area. However, it is within the scope of this disclosure to have a first flat surface and second flat surface with differing shape, size and surface area.

For example, if first and second flat surfaces 216 and 218 are rectangular having a length along edge 220 of 10 cm and a width along edge 222 of 4 cm, each of surfaces 216 and 218 would have a surface area of 40 cm$^2$; thus, the separation of the first and second flat surfaces 216 and 218 could be 4 mm or less, 3 mm or less, or 2 mm or less. However, the flat surfaces do not have to be rectangular. Any other suitable shape can be used, for example, a semicircular or oblong shaped flat surface can be used. Typically, however, first flat surface 216 and second flat surface 218 will be matching.

Such a design allows cell 200 to have parallel electrically conducting plates 224 and 226 of similar surface area and separation to the first and second flat surfaces 216 and 218. Generally, the two conducting plates 224 and 226 will be referred to herein as each being the same size and shape as the first surface and second surface 216 and 218, which as used herein means that the two plates are small enough to be received within the second chamber 214 but are of similar size to the first surface and second surface 216 and 218; that is, from 90% to 99.9% of the size. As will be realized, the walls 202, 204, 206 and 208 are made of a non-conducting material so as not to short out plates 224 and 226.

As an example, rectangular first and second flat surfaces and the conducting plates 224 and 226 could each have a surface area of about 40 cm$^2$ with a length of 10 cm, a width of 4 cm and a separation between the conducting plates of 1.6 mm or less. More generally, in some embodiments, the first and second flat surfaces 216 and 218 can each have a surface area of 100 cm$^2$ or less, 80 cm$^2$ or less, 60 cm$^2$ or less, 50 cm$^2$ or less, or even 45 cm$^2$ or less. The first and second flat surface can have a minimum surface area of 10 cm$^2$, 15 cm$^2$, or 20 cm$^2$. Also, the separation of the first and second flat surfaces can be 10 mm or less, 8 mm or less, 5 mm or less, 3 mm or less, 2 mm or less, or even 1.6 mm or less. As will be realized from the above, plates 224 and 226 also can have typically an area of 100 cm$^2$ or less, 80 cm$^2$ or less, 60 cm$^2$ or less, 50 cm$^2$ or less, or even 45 cm$^2$ or less, and can have a minimum surface area of 10 cm$^2$, 15 cm$^2$, or 20 cm$^2$. Also, the separation of the plates 224 and 226 can be 10 mm or less, 8 mm or less, 5 mm or less, 3 mm or less, 2 mm or less, or even 1.6 mm or less.

The cell constant of an EIS cell is dependent on the surface area and spacing of the electrical plates. The above dimensions provide for an EIS cell with a suitable cell constant; however, other designs that achieve a cell constant of less than 1 cm$^{-1}$ are within the scope of this disclosure.

Figure 4:
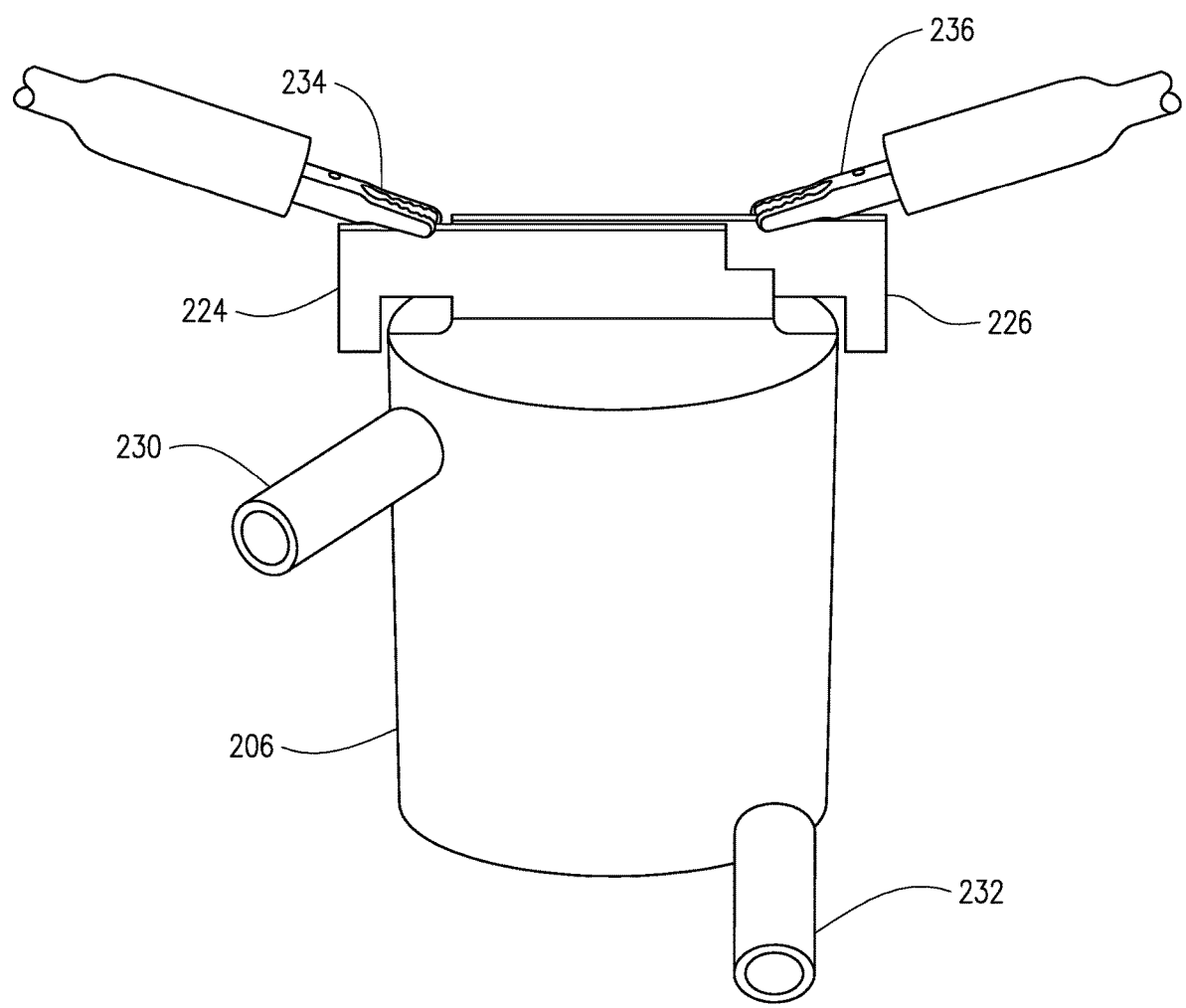
FIG. 4 is a front view picture of an EIS cell in accordance with some embodiments of this disclosure.
Figure 5:
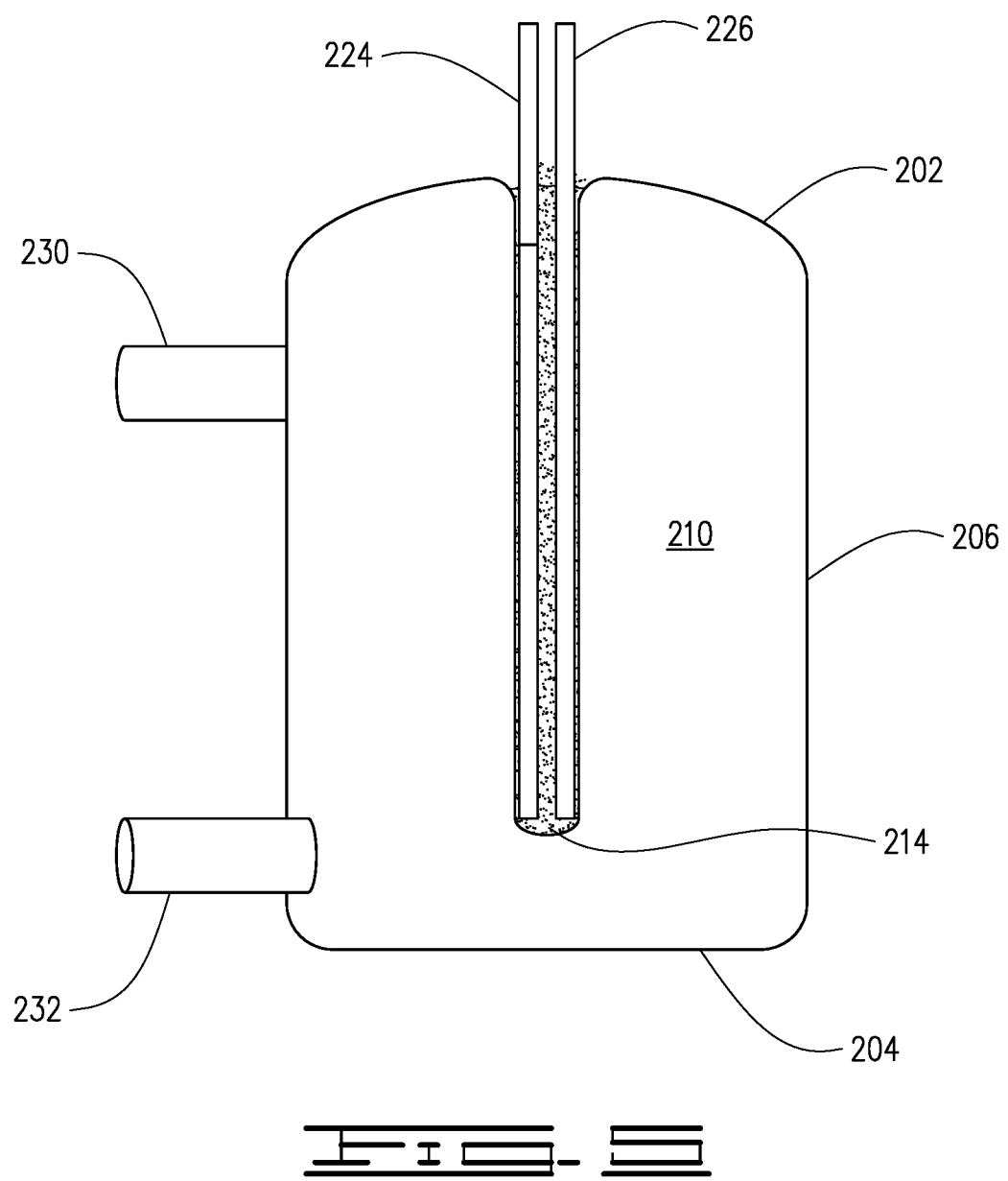
FIG. 5 is a side view picture of the EIS cell of FIG. 4.

As can be seen best from FIG. 4, electrically conducting plate 224 is connected to a first electrode 234 and electrically conducting plate 226 is connected to a second electrode 236 during EIS testing such that a current can be passed through the plates and the test fluid within second chamber 214 and the impedance of the test fluid thus measured.

Returning to the first chamber 210, it can be designed to hold a fluid; more typically, first chamber 210 contains a flowing fluid. Generally, the fluid is used to control the temperature in second chamber 214. Fluid flow into and out of the first chamber 210 is through an upper port 230 and a lower port 232; that is either in through lower port 232 and out through upper port 230, or in through upper port 230 and out through lower port 232. Often the flow into and out of first chamber 210 will be only through first and second ports 230 and 232; that is, there can be no other such ports. As illustrated, outer wall 206 of cell 200 defines upper port 230 and lower port 232. Upper port 230 is positioned higher on the outer wall than lower port 232. Preferably, upper port 230 is adjacent to top wall 202 and lower port 232 is adjacent to bottom wall 204. Further, upper port 230 is spaced about outer wall 206 so as not to be in vertical alignment with lower port 232. Preferably, the two ports are spaced circumferentially from each other so as to be at least 30° apart. Upper port 230 and lower port 232 are positioned so that fluid introduced through either the upper port or lower port enters first chamber 210 tangentially to the outer wall 206. This arrangement of the ports ensures that first chamber 210 is filled with fluid with a minimum of stagnant areas. Generally, fluid can be flowed through first chamber 210 to control the temperature within second chamber 214.

An EIS cell designed in accordance with this disclosure can have a small well volume—the volume of second chamber 214—compared to prior EIS cells. For example, in one design, first and second flat surfaces 216 and 218 had a combined surface area of approximately 84 cm² and a separation of 1.58 mm; thus, the well volume was about 13.3 ml, and once plates 224 and 226 were added, the well volume was about 12 ml. Accordingly, an EIS cell designed in accordance with this disclosure can have a well volume of 100 ml or less, and more typically will have a well volume of 50 ml or less, 30 ml or less, 20 ml or less or 15 ml or less.

In assessing the level of sensitivity of an EIS cell, the cell constant is a useful parameter. The cell constant is a conversion factor which relates to conductance in an EIS cell and the fluid conductivity which is contained within it. The cell constant of an EIS cell can be expressed by the equation:

$$\kappa = \frac{1}{a} = KR$$

where Kappa ($\kappa$) is the cell constant, K is the specific conductance, and R is the measured resistance. To solve for a specific cell constant, the equation $\sigma = \kappa G$ is employed. G is the conductance of the cell in Siemens, $\kappa$ is the cell constant in reciprocal centimeters, and $\sigma$ is the specific conductance of the solution being measured in Siemens reciprocal centimeters. By performing electrochemical impedance spectroscopy of an electrolytic solution with varying, known concentrations at a fixed temperature, the cell constant can be determined. The bulk resistivity value is obtained from the EIS data and its reciprocal gives G, from the expression above.

Conventional EIS cells have a cell constant of greater than 1 cm$^{-1}$; however, EIS cells in accordance with the current design generally have a constant of less than 1 cm$^{-1}$, and more typically, have a cell constant of 0.5 cm$^{-1}$ or less, or 0.1 cm$^{-1}$ or less, or 0.05 cm$^{-1}$ or less. Due to the current EIS cell's small cell constant, it is possible to measure, not only the impedance of crude oil, but also that of highly resistive condensate and model oil systems, which would otherwise be unmeasurable by conventional EIS cells.

EXAMPLES

The above methods and apparatuses, and systems incorporating them, can be better understood by the following examples, which support and illustrate various embodiments.

Example 1—Cell Design

A conventional commercially-available EIS cell was tested to experimentally determine cell constant. The cell was designed to utilize circular platinum electrodes according to conventional EIS processes. The electrodes had a surface area of 0.79 cm² within a well volume of 20 ml.

The cell constant was found using a KCl solution at 25° C. in DI H2O. The standard conductivity values were: 0.01 M=1408.230 μScm$^{-1}$, 0.1 M=12,824.6 μScm$^{-1}$, 1.0 M=108, 620 μScm$^{-1}$. Based on the molar mass of KCl, the final cell constant was $\kappa$=3.64 cm$^{-1}$.

A design in accordance with this disclosure was also tested to experimentally determine the cell constant. In the design, the electrically conductive plates were made of 316 stainless steel and had a combined surface area of approximately 84 cm² and a separation of 1.58 mm. The well volume was about 12 ml once the plates were added to the well. The cell constant was found using KCL solution at 25° C. in DI H$_2$O using the same method as was used for the conventional cell. For the cell design in accordance with this disclosure, the final cell constant was $\kappa$=0.02 cm$^{-1}$.

This relatively small cell constant is desirable for measuring poorly conducting systems (i.e. highly resistive systems). The new cell has a cell constant 182 times smaller than the conventional EIS cell, which correlates to being able to measure systems with much higher resistivities than could be measured with the conventional cell design.

Example 2—Method

A paraffin inhibitor was added to crude oil in various amounts to produce five samples: a neat sample having 0 ppm of the paraffin inhibitor; a 1$^{st}$ treated sample having 250 ppm of the paraffin inhibitor; a 2$^{nd}$ treated sample having 500 ppm of the paraffin inhibitor; a 3$^{rd}$ treated sample having 1000 ppm of the paraffin inhibitor; and a 4$^{th}$ treated sample having 2000 ppm of the paraffin inhibitor. The paraffin inhibitor was a copolymer amide in a non-polar organic solvent package as is referred to herein by the designation PI 800.

The WAT of the crude oil was approximately 21° C. Impedance for each sample was measured using EIS at 35° C. (a temperature above the WAT) and at 15° C. (a temperature below the WAT). For each treated sample, a complete data set included the impedance measurements above and below WAT for the treated sample and the impedance measurements above and below the WAT for the neat sample. Thus, one complete data set for one of the treated samples is comprised of an EIS measurement above the crystallization temperature with no paraffin inhibitor added, referred to as Above-Neat (AN), an EIS measurement below the crystallization temperature with no paraffin inhibitor added, referred to as Below-Neat (BN), and two more tests at the same temperatures with a given concentration of a paraffin inhibitor, referred to as Above-Treated (AT) and Below-Treated (BT).

The EIS impedance measurement is a complex number; thus, a Nyquist plot was used to resistance values. An example Nyquist plot for the neat sample and $2^{nd}$ treated sample (500 ppm of paraffin inhibitor) is illustrated in FIG. 7. In order to assess the paraffin inhibitor's performance, the right most point on the Nyquist plots are used as the resistance values. Thus, based on FIG. 7, the resistance values of the data set for the $2^{nd}$ treated sample are shown in Table 2.

TABLE 2

| EIS Measurement Conditions | Resistance Values |
|---|---|
| AT-Above WAT for $2^{nd}$ Treated Sample | 2.5797E10 |
| BT-Below WAT for $2^{nd}$ Treated Sample | 5.3447E10 |
| AN-Above WAT for Neat Sample | 5.1245E10 |
| BN-Below WAT for Neat Sample | 12.209E10 |

Next the resulting resistance values were normalized using:

$$BN^* = BN;$$

$$AN^* = AN(BN/AN) = BN;$$

$$AT^* = AT(BN/AN), \text{ and}$$

$$BT^* = BT(AN/AT),$$

Wherein BN, AN, AT and BT are the impedance measurements and BN*, AN*, AT* and BT* are the normalized impedance measurement. The resulting normalized values for the data set related to the $2^{nd}$ treated sample are shown in Table 3.

TABLE 3

| EIS Measurement Conditions | Resistance Values | Normalized Resistance Values |
|---|---|---|
| AT for 2nd Treated Sample | 2.5797E10 | 6.1461E10 |
| BT for 2nd Treated Sample | 5.3447E10 | 10.6171E10 |
| AN for Neat Sample | 5.1245E10 | 12.209E10 |
| BN for Neat Sample | 12.209E10 | 12.209E10 |

Finally, the performance of the paraffin inhibitor at a given concentration (EPIPS) was calculated based on the percent differences of the normalized values using:

$$\Delta A = abs(AN^* - AT^*)/((AN^* + AT^*)/2);$$

$$\Delta B = abs(BN - BT^*)/((BN + BT^*)/2); \text{ and}$$

$$EPIPS = \Delta A - \Delta B.$$

The results of the above calculations for the data set related to the $2^{nd}$ treated sample is shown in Table 4 and the EPIPS results for all four of the treated sample data sets are shown in Table 5.

TABLE 4

| $2^{nd}$ Treated Sample Data Set (PI 800) | Calculated Values |
|---|---|
| ΔA | 0.1395 |
| ΔB | 0.6606 |
| EPIPS | 0.5211 |

TABLE 5

| Treated Sample Data Set | EPIPS (PI 800) |
|---|---|
| Neat Sample-0 ppm paraffin inhibitor | 0 |
| $1^{st}$ Treated Sample-250 ppm paraffin inhibitor | 0.327 |
| $2^{nd}$ Treated Sample-500 ppm paraffin inhibitor | 0.521 |
| $3^{rd}$ Treated Sample-1000 ppm paraffin inhibitor | 0.751 |
| $4^{th}$ Treated Sample-2000 ppm paraffin inhibitor | 0.697 |

Table 5 verifies the validity of the current method because when applied to an untreated (0-ppm) system, the resultant EPIPS value is zero, as expected. Also, the EPIPS increases as more inhibitor is added (to a point), since if the polymer in the paraffin inhibitor is targeting the paraffin in the system, as more paraffin inhibitor is added, more will be incorporated into the wax crystals until they are saturated.

The method was further verified by carrying out the above method for two different paraffin inhibitors: PI 000 and PI 801. PI 000 was a cumene in a non-polar, organic solvent package, and PI 801 was an organic sulfonic acid and fatty acid amide in a non-polar, organic solvent package.

A cold finger test was also performed for the three paraffin inhibitors to determine performance. The cold finger test was performed on the crude oil injected with the three paraffin inhibitors at various concentrations: PI 800 at 0, 250, 500, and 1000 ppm; PI 000 at 0, 250, 500, and 1000 ppm; and PI 801 at 0, 250, 500, 1000, and 2000 ppm. The bulk temperature was set to 30° C., the finger temperature set to 5° C., with a bulk fluid stir rate of 600 RPM. These conditions were held for 8 hours, and the resultant deposit was then weighed.

The predicted performance determination from the current method (EPIPS) and the actual performance from the cold finger test (PIE) are shown in FIG. 8 for each of the paraffin inhibitors. As shown, the predicted performance and actual paraffin inhibitor performance differ by no more than 5%, and the experimental error range of the cold finger test is around +/−4%. They have excellent agreement.

Example 3—Method

The method was further verified by carrying out the same method as described for Example 2 for a light-shale crude condensate. For this Example 3, only the PI 800 and PI 000 paraffin inhibitors were used.

The two paraffin inhibitors were added to the crude condensate in various amounts similar to Example 2 to produce five samples for each paraffin inhibitor: a neat sample having 0 ppm of the paraffin inhibitor; a 1st treated sample having 250 ppm of the paraffin inhibitor; a 2nd treated sample having 500 ppm of the paraffin inhibitor; a 3rd treated sample having 1000 ppm of the paraffin inhibitor; and a 4th treated sample having 2000 ppm of the paraffin inhibitor. As indicated, the paraffin inhibitors were the copolymer amide in a non-polar organic solvent package referred to by the designation PI 800, and the cumene in a non-polar, organic solvent package referred to by the designation PI 000.

The WAT of the crude condensate was approximately 34° C. Impedance for each sample was measured using EIS at 45° C. (a temperature above the WAT) and at 15° C. (a temperature below the WAT).

The cold finger test was also performed for the crude condensate samples. The cold finger test was performed on the crude condensate with paraffin inhibitor at various concentrations: PI 800 at 0, 250, 500, 1000 and 2000 ppm; and PI 000 at 0, 250, 500, 1000 and 2000 ppm. The bulk temperature was set to 30° C., the finger temperature set to 5° C., with a bulk fluid stir rate of 600 RPM. These conditions were held for 8 hours, and the resultant deposit was then weighed.

The predicted performance determination from the current method (EPIPS) and the actual performance from the cold finger test (PIE) are shown in FIG. 9 for each of the paraffin inhibitors. As shown, the predicted performance and actual paraffin inhibitor performance have excellent agreement.

The apparatuses, systems and methods of the current disclosure have been described in reference to the specific embodiments described and illustrated in the figures; however, the embodiments are not meant to be limited to those specific embodiments. As will be apparent to those skilled in the art, features of one embodiment are capable of being used in one of the other embodiments as long as they do not directly conflict with elements of the other embodiment.

While methods are described in terms of "comprising," "containing," or "including" various components or steps, the compositions and methods also can "consist essentially of" or "consist of" the various components and steps. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent(s) or other documents that may be incorporated herein by reference, the definitions that are consistent with this specification should be adopted.

What is claimed is:

1. A method comprising:
   measuring impedance of an oil containing a paraffin so as to obtain at least four impedance measurements, wherein the impedance measurements include:
   a BT impedance measurement, wherein the BT impedance measurement is for a treated sample of the oil sample which contains a paraffin inhibitor, and wherein the impedance is measured at a first temperature below the wax appearance temperature (WAT) of the paraffin;
   a BN impedance measurement, wherein the BN impedance measurement is for a neat sample of the oil which does not contain the paraffin inhibitor, and wherein the impedance is measured at the first temperature;
   an AT impedance measurement, wherein the AT impedance measurement is for the treated sample, and wherein the impedance is measured at a second temperature above the WAT of the paraffin; and
   an AN impedance measurement, wherein the AN impedance measurement is for the neat sample, and wherein the impedance is measured at the second temperature;
   determining from the impedance measurements a set of impedance values which allows for comparison so as to determine paraffin inhibitor performance; and
   comparing the set of impedance values to determine paraffin inhibitor performance.

2. The method of claim 1, wherein the set of impedance values are determined by normalizing one or more of the impedance measurements, wherein the normalization allows for comparison by compensating for changes to impedance caused by temperature change, by introduction of paraffin inhibitor or by both.

3. The method of claim 2, wherein the AN impedance measurement and AT impedance measurements are normalized relative to a ratio of the BN impedance measurement and AN impedance measurement to compensate for temperature, and the BT impedance measurement is normalized relative to a ratio of the AN impedance measurement and AT impedance measurement to compensate for paraffin inhibitor introduction.

4. The method of claim 1, wherein the measuring impedance is by potentiometric electrochemical impedance spectroscopy.

5. The method of claim 1, wherein there are multiple treated samples of the oil with each such sample having a different concentration of paraffin inhibitor and wherein the BT impedance and AT impedance are measured for each of the treated samples.

6. The method of claim 5, wherein the comparison results in a predicted paraffin performance for each concentration of paraffin inhibitor to produce a set of predicted paraffin performances and wherein the predicted paraffin performances are analyzed to determine an optimal concentration of paraffin inhibitor for the oil.

7. The method of claim 6, wherein the measuring impedance is by potentiometric electrochemical impedance spectroscopy.

8. The method of claim 7, wherein the set of impedance values are determined by normalizing one or more of the impedance measurements, wherein the normalization allows for comparison by compensating for changes to impedance caused by temperature change, by introduction of paraffin inhibitor or by both.

9. The method of claim 8, wherein the AN impedance measurement and AT impedance measurements are normalized relative to a ratio of the BN impedance measurement and AN impedance measurement to compensate for temperature, and the BT impedance measurement is normalized relative to a ratio of the AN impedance measurement and AT impedance measurement to compensate for paraffin inhibitor introduction.

* * * * *